United States Patent [19]
Walsh

[11] Patent Number: 6,117,116
[45] Date of Patent: *Sep. 12, 2000

[54] INTUBATION OF LACRIMAL DUCTS

[75] Inventor: David J. Walsh, Waterdown, Canada

[73] Assignee: Walsh Medical Devices Inc., Oakville, Canada

[ * ] Notice: Under 35 U.S.C. 154(b), the term of this patent shall be extended for 495 days.

[21] Appl. No.: 08/561,658

[22] Filed: Nov. 22, 1995

[51] Int. Cl.[7] .................................................... A61M 5/00
[52] U.S. Cl. ................................ 604/264; 604/8; 604/523
[58] Field of Search ................................. 604/8–10, 175, 604/264, 280, 285, 289, 290, 294, 103, 523; 128/772; 403/28, 273; 285/381.4; 174/21 R; 600/585

[56] References Cited

U.S. PATENT DOCUMENTS

| | | |
|---|---|---|
| 2,154,968 | 4/1939 | Alkio . |
| 3,948,272 | 4/1976 | Guibor . |
| 4,305,395 | 12/1981 | Martinez . |
| 4,380,239 | 4/1983 | Crawford et al. . |
| 4,658,816 | 4/1987 | Ector, Jr. . |
| 5,195,969 | 3/1993 | Wang et al. ............................... 604/96 |
| 5,405,329 | 4/1995 | Durand .................................... 604/164 |
| 5,437,625 | 8/1995 | Kurihashi ..................................... 604/8 |

*Primary Examiner*—Corrine McDermott
*Assistant Examiner*—Cris L. Rodriguez
*Attorney, Agent, or Firm*—Ingrid E. Schmidt

[57] ABSTRACT

The invention provides a probe set having at least one probe of a light wire which can be resiliently deflected to pass from the nasolacrimal duct to the nasal inferior meatus. The probe has an enlarged and rounded distal end portion to limit the possibility of damage to tissue when the probe is inserted. A very flexible tube of minimal rigidity is engaged over a proximal end of the probe and a heat shrunk sleeve is attached to join the tube to the probe. Preferably the sleeve has a main portion containing a first end portion containing part of the probe adjacent the tube, a second end portion containing a part of the tube adjacent said end of the probe, and a main portion containing the ends of the probe and the tube. The sleeve applies a compressive radial pressure to attach the tube to the probe and defines a transition portion between the first end portion and the main portion of the sleeve to minimise the possibility of snagging as the probe set is advanced into the lacrimal duct. The probe set preferably includes a second probe at the other end of the tube.

18 Claims, 1 Drawing Sheet

INTUBATION OF LACRIMAL DUCTS

FIELD OF THE INVENTION

This invention relates to an improved device which is particularly useful in the intubation of the lacrimal ducts.

BACKGROUND OF THE INVENTION

Lacrimal fluid (commonly called "tears") is normally supplied continuously to the human eye from the lacrimal gland. Excess fluid drains through canaliculi or small passageways commencing adjacent the inner corner of the eye. Fluid collects in the lacrimal sac before draining via the nasolacrimal duct into the inferior nasal meatus. For the purposes of this disclosure, the passages forming the drainage system will be referred to collectively as the lacrimal ducts.

Some medical conditions can arise where lacrimal ducts become blocked so that fluid can no longer flow to the nasal meatus. These conditions include congenital anomalies, accidents, inflammation and advanced aging, as well as other physiological conditions. The result is that the eye is continually brimming over with fluid causing much personal discomfort to the patient.

Several devices have been proposed for correcting blocked lacrimal ducts. One is described in U.S. Pat. No. 2,154,968 to Alkio which issued in 1939. This patent teaches a structure consisting of several parts including a rigid tubular probe which contains a very flexible fine wire. The end of the wire is enlarged to retain the wire in the tube and the probe is inserted through the lacrimal duct until it projects into the inferior meatus of the nose. Then, by withdrawing the tube partially, the wire can be withdrawn through the meatus using a tool which traps the enlarged end of the wire. The flexibility of the wire permits the wire to bend with minimal resistance where the nasolacrimal duct meets the inferior meatus. A spiral canula is then slipped up the wire and into the lacrimal duct so that the wire can subsequently be withdrawn upwardly leaving the spiral canula in place.

A second structure was proposed by Dr. P. Guibor who presented a new device at the 79th Annual Meeting of the American Academy of Oxology and Otolaryngology which was held in Dallas, Tex. on Oct. 6–10 of 1974. Dr. Guibor described a structure consisting of a pair of quite stiff stainless steel probes that attach one to each end of a length of Silastic tubing (trade mark of Dow Corning). The tubing is attached to end portions of the probe which are of tempered stainless steel with sufficient stiffness to ensure that the arched shape of the probes tends to maintain its shape in use. In this respect, Dr. Guibor's structure has a similarity to the Alkio structure because in both structures the probe is quite stiff and is designed to retain its shape as it is pushed downwardly into the lacrimal duct. This stiffness was apparently considered to be necessary in such devices and is in marked contrast with a further prior art structure shown in U.S. Pat. No. 4,380,239 which issued on Apr. 19, 1983 to Dr. John Crawford et al.

Dr. Crawford's structure provided a probe set consisting of a light wire which can be readily deflected through an angle of at least 90° to permit the probe to pass from the nasolacrimal duct to the inferior meatus. The probe has an enlarged end portion which is rounded to limit the possibility of damage to tissue when the probe is inserted, and a very flexible tube of minimal rigidity having a first end attached to the probe remote from the end portion and having an outside diameter comparable to that of the end portion. In use the probe can be inserted and used to draw the tube into the lacrimal duct. The enlarged end is also used to draw the device through the lacrimal duct by using the hook shown in the Crawford patent.

While Dr. Crawford's device has achieved significant commercial success, it is an object of the present invention to provide an improved structure, and more particularly an improved structure using the principles taught in Crawford et al U.S. Pat. No. 4,380,239.

The structure taught by Dr. Crawford et al also includes an enlargement where the probe is attached to the tubing. The enlargement has a diameter matching that of the tubing so that the tubing can be pushed onto the wire and into engagement with the enlargement. As a result, as the wire is drawn through the lacrimal duct, the enlargement protects the end of the tube and prevents a load being applied to the tube tending to separate the tube from the probe.

Such an arrangement has been proven to be commercially successful but the difficulty of preparing a probe of this kind with the enlargement positioned on the probe, has increased the cost of manufacture.

A further disadvantage of the structure taught by Dr. Crawford is the stress concentration that can be developed where the tube meets the probe. The tube is extremely flexible and can be pulled at right angles to the direction of the probe without significantly bending the probe. This can result in tearing the tube due to the build up in stress in the tube where it meets the probe.

Such disadvantages of the prior art are addressed in the present invention.

SUMMARY OF THE INVENTION

In one of its aspects, the invention provides a probe set having at least one probe of a light wire which can be resiliently deflected to pass from the nasolacrimal duct to the nasal inferior meatus. The probe has an enlarged and rounded end portion to limit the possibility of damage to tissue when the probe is inserted.

A very flexible tube of minimal rigidity is engaged over an end of the probe and a heat shrunk sleeve is attached to join the tube to the probe. Preferably the sleeve has a first end portion containing part of the probe adjacent the tube, a second end portion containing a part of the tube adjacent said end of the probe, and a main portion containing the ends of the probe and the tube. The sleeve applies a compressive radial pressure to attach the tube to the probe and defines a transition portion between the first end portion and the main portion of the sleeve to minimise the possibility of snagging as the probe set is advanced into the lacrimal duct.

The probe set preferably includes a second probe at the other end of the tube.

DESCRIPTION OF THE PREFERRED EMBODIMENT(S)

Figure 1:
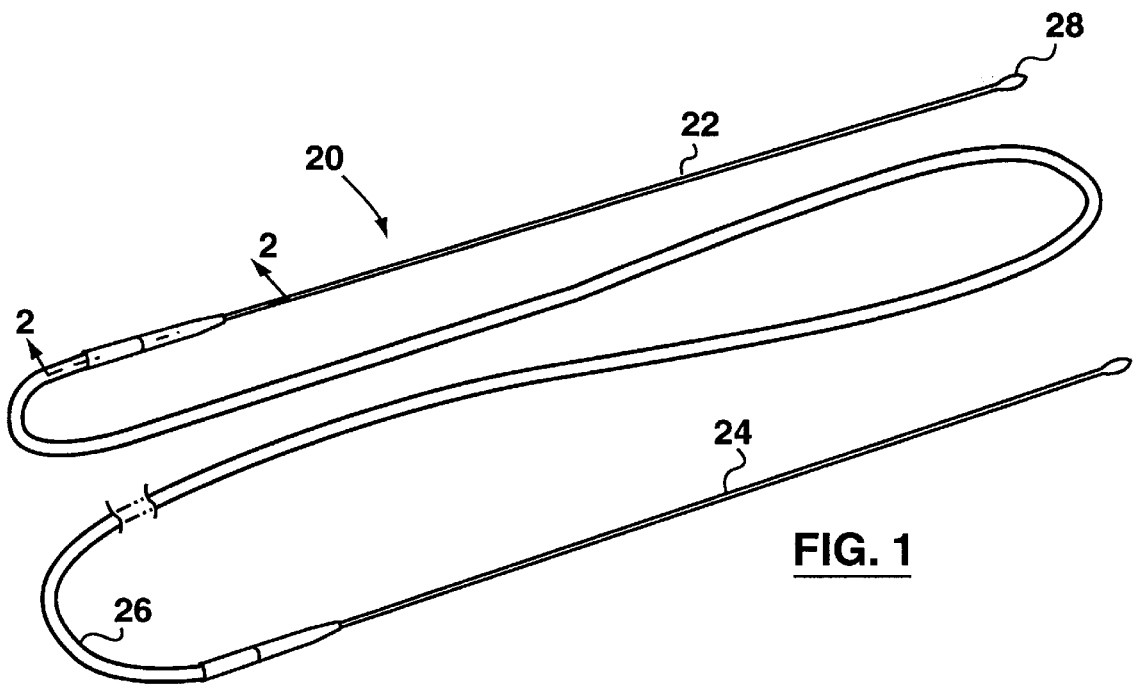
FIG. 1 is a view of a probe set incorporating a preferred embodiment of the invention.

Reference is first made to FIG. 1 which illustrates a probe set designated generally by the numeral 20 and illustrating a preferred embodiment of the invention. The probe set consists essentially of a pair of thin probes 22,24 fitted to respective ends of a tube 26 of silicone rubber which by its nature is limp and very flexible.

The probe 22 is typical also of probe 24 and includes an enlarged distal end portion 28 and is connected to the tube 26 at a joint structure 30. The enlarged end portion 28 is rounded and somewhat spherical and exhibits a maximum transverse cross-section comparable to that of the joint 30. The preferred probes 22,24 are formed from a relatively fine steel wire having a diameter of about 0.4 mm and a length of about 12 cm. The probe has a small resistance to deflection but is tempered so that it tends to retain is original shape after being subjected to small deflections.

The probe will move through the lacrimal duct when pushed downwardly and will tend to follow the shape of the duct. Such a fine wire would of course puncture tissue if the end of the wire did not include the enlarged end portion 28 to cover the end of the wire.

The tube 26 is preferably of silicone rubber having an outside diameter of about 0.6 mm and an internal diameter of about 0.3 mm. (Preferred tubing is medical grade silicone tubing.) It would be appreciated from the above dimensions that the tubing 16 can be pushed over the ends of the probes where, if preferred, as a first step to the assembly of the joint 30, the tube can be bonded to the probe using a suitable adhesive.

To this point in the description, the probes 22,24 and tube 26 are somewhat similar to that as described in Dr. Crawford's aforementioned patent. However, the inventive joint 30 differs from that previously used and will be described with reference to FIG. 2.

Figure 2:
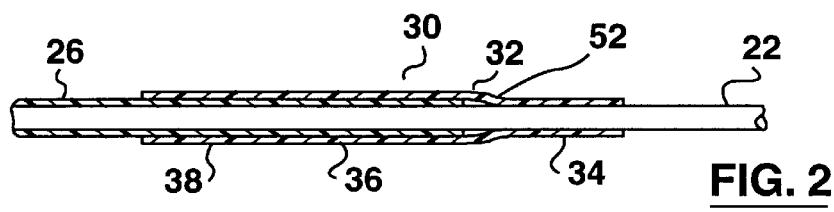
FIG. 2 is a sectional view on line 2—2 of FIG. 1 and drawn to a larger scale than FIG. 1 to illustrate a joint.

As seen in FIG. 2, a proximal end of the probe 22 is engaged in one end of the tube 26. The view is not drawn to scale because of the very small dimensions used in these parts. In fact, the tube 26 is typically engaged over the probe 22 to the extent of about 1.75 cm. The joint 30 also includes a heat shrunk sleeve 32 which is typically about 3 cm long and includes a first end portion 34 tightly engaged on the probe 22, and a main portion 36 engaged over the tube 26 to apply radial compressive force on the limp tube 26. The sleeve also extends to a second end portion 38 which extends over the tube where the tube is free of the probe 22 to provide a collar to support the tube 26 as will be described with reference to FIG. 3.

The heat shrunk sleeve 30 is made from tetrafluoroethylene having an original inside diameter of about 0.46 mm and a wall thickness of about 0.05 mm. As mentioned previously, the tube 26 can be attached to the probe 22 using any suitable adhesive but this is not necessary in most situations due to the compressive loading by the sleeve 30 on both the probe 22 and the tube 26 where the tube contains the probe. Its been found that the joint 30 in this form is adequate for proper use of the probe set.

Figure 3:
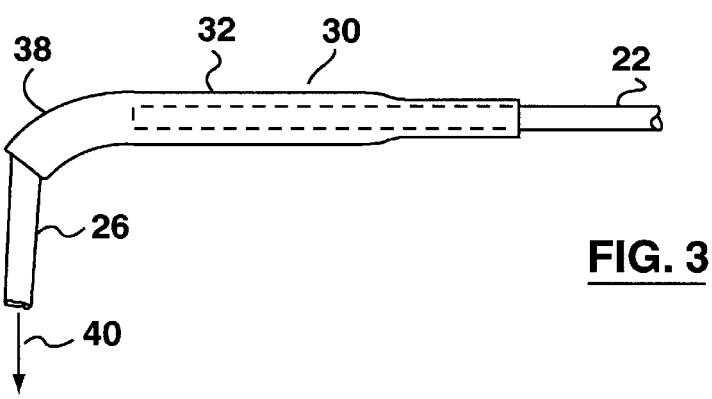
FIG. 3 is a side view of the joint and showing how transverse load bends the structure.

Reference is next made to FIG. 3 which illustrates the sleeve 30 after assembly and subjected to a side load. The load is in a direction of the arrow 40 which is transverse relative to the axis of the probe 22. The result is that the limp tube 26 (which would have no resistance to deformation) is supported by the second end portion 38 of the sleeve 32 between the end of the probe and the end of the portion 38. This portion will take a generally curved form (unless it is pulled extremely vigorously) and is in effect a reinforcement to prevent the tube 26 from being drawn at right angles to the end of the probe 22 at the end of the probe.

Figure 4:
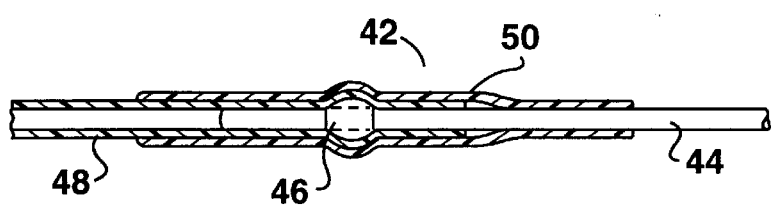
FIG. 4 is a view similar to FIG. 2 and illustrating an alternative embodiment of the invention.

Reference is next made to FIG. 4 which illustrates an alternative embodiment providing further strength against a separation at a joint 42 similar in most respects to joint 30. However, the joint 32 is formed around a probe 44 which has an enlargement 46 preferably in the form of an olive soldered to the probe and defining a generally spherical shape over which a tube 48 has been engaged. A sleeve 50 produces a radial compressive force which, because of the shape of the olive 46, is concentrated around the olive to provide a further resistance to separation of the tube 48 from the probe 44.

The probe set will be used in the manner described in the aforementioned U.S. Pat. No. 4,380,239 to Dr. Crawford. As a result of Dr. Crawford's invention the procedure has become well used and is consequently now a well known procedure. The tool described in that patent can be used with the present probe set.

The probe set 20 exhibits different characteristics when being drawn into the lacrimal duct. As better seen in FIG. 2, the sleeve 30 is tightly engaged on the probe 22 at the first end portion 34, and also on the tube 26 at the main portion 36. As the probe set is inserted, the portion 34 will enter first and the duct will be enlarged slightly to accommodate the end of the sleeve. Next the main portion must enter and this portion represents a significant enlargement due to the presence of the end of the tube 26. One of the advantages of the present invention is that the sleeve 32 provides a smooth tapered transition portion 52 from the smaller end portion 34 to the main portion 36. Consequently, as the probe set is advanced in the duct, the transition portion 52 will ensure that the movement is smooth and free of snags.

The embodiment shown in FIG. 4 will operate in a similar fashion with slight enlargement caused by the olive 46 causing a temporary dilation as it progresses through the lacrimal duct. It will of course be evident that the shape of the olive is chosen to ensure smooth dilation which is kept to a minimum. However any equivalent structure such as a flattening or deformation of the wire will assist the action of the heat-shrinkable tubing at the joint and all such structures are intended to be within the scope of the term "olive".

The invention has been described with reference to preferred embodiments. Other embodiments and equivalent structures incorporating the invention are within the scope of the invention as claimed.

What is claimed is:

1. A probe set for use in the canaliculus intubation of the lacrimal duct, the probe set comprising:

a probe of a light wire which can be resiliently deflected to pass from the nasolacrimal duct to the nasal inferior meatus, the probe having an enlarged and rounded distal end portion to limit the possibility of damage to tissue when the probe is inserted, and a proximal end remote from said end portion;

a very flexible tube of minimal rigidity, the tube also being resiliently deformable and having a first end; and a joint including said first end of the tube with said proximal end of the probe contained in said first end of the tube, and a heat shrunk sleeve having a main portion containing said end of the tube and said proximal end of the probe whereby a compressive radial pressure is applied to attach the tube to the probe.

2. A probe set as claimed in claim 1 in which the sleeve further includes an end portion containing part of the probe adjacent the tube.

3. A probe set as claimed in claim 1 in which the sleeve further includes an end portion containing a part of the tube adjacent said proximal end of the probe.

4. A probe set as claimed in claim 3 in which said end portion of the sleeve supports the tube to reduce stress in the tube when the tube is pulled transversely relative to the probe.

5. A probe set as claimed in claim 3 and further comprising a second probe and second joint, the second joint attaching the second probe to the tube at an end of the tube remote from said first end.

6. A probe set as claimed in claim 5 in which the probes are similar.

7. A probe set as claimed in claim 1 in which the sleeve further includes a first end portion containing part of the probe adjacent the tube, and a second end portion containing a part of the tube adjacent said end of the probe.

8. A probe set as claimed in claim 4 in which the probe is of stainless steel wire having a diameter of about 0.4 m.

9. A probe set as claimed in claim 8 in which the tube is of silicone rubber.

10. A probe set as claimed in claim 7 and further comprising a transition portion between said main portion and said first end portion, the transition portion minimising the possibility of snagging as the probe set is advanced into the lacrimal duct.

11. A probe set for use in the canaliculus intubation of the lacrimal duct, the probe set comprising:

a probe of a light wire which can be resiliently deflected to pass from the nasolacrimal duct to the nasal inferior meatus, the probe having an enlarged and rounded distal end portion to limit the possibility of damage to tissue when the probe is inserted, and a proximal end remote from the distal end portion;

a very flexible tube of minimal rigidity, the tube also being resiliently deformable and having a first end engaged over said end of the probe; and a heat shrunk sleeve having a main portion containing said end of the tube and said end of the probe, a first end portion containing part of the probe adjacent the tube, and a second end portion containing a part of the tube adjacent said proximal end of the probe, the sleeve applying a compressive radial pressure to attach the tube to the probe and defining a transition portion between the first end portion and the main portions of the sleeve to minimise the possibility of snagging as the probe set is advanced into the lacrimal duct.

12. A probe set as claimed in claim 11 in which said second end portion of the sleeve supports the tube to reduce stress in the tube when the tube is pulled transversely relative to the probe.

13. A probe set as claimed in claim 11 and further comprising a second probe and second sleeve, the second sleeve attaching the second probe to the tube at an end of the tube remote from said first end.

14. A probe set as claimed in claim 13 in which the probes are similar.

15. A probe set as claimed in claim 11 in which the probe is of tempered stainless steel wire having a diameter of about 0.4 mm.

16. A probe set as claimed in claim 15 in which the tube is of silicone rubber.

17. A probe set for use in the canaliculus intubation of the lacrimal duct, the probe set comprising:

a probe of a light wire which can be resiliently deflected to pass from the nasolacrimal duct to the inferior nasal meatus, the probe having an enlarged and rounded distal end portion to limit the possibility of damage to tissue when the probe is inserted, and a proximal end remote from said end portion;

a very flexible tube of minimal rigidity, the tube also being resiliently deformable and having a first end; and a joint including said first end of the tube with said proximal end of the probe contained in said first end of the tube, said joint further including a heat shrunk sleeve having a main portion containing said end of the tube and said proximal end of the probe, said sleeve further including a first end portion containing part of the probe adjacent the tube, and a second end portion containing a part of the tube adjacent said end of the probe; and an enlargement to the probe adjacent said proximal end of the probe and contained within said main portion of the sleeve; whereby and enhanced compressive radial pressure is applied to attach the tube to the probe.

18. A probe set as claimed in claim 17 in which the enlargement is an olive soldered to the probe.

* * * * *